(12) United States Patent
Oh

(10) Patent No.: US 11,590,249 B1
(45) Date of Patent: Feb. 28, 2023

(54) PORTABLE ILLUMINATION APPARATUS HAVING STERTLIZING FUNCTION

(71) Applicant: IRTRONIX, INC., Torrance, CA (US)

(72) Inventor: Danny Oh, Torrance, CA (US)

(73) Assignee: IRTRONIX, INC., Torrance, CA (US)

( * ) Notice: Subject to any disclaimer, the term of this patent is extended or adjusted under 35 U.S.C. 154(b) by 0 days.

(21) Appl. No.: 17/463,296

(22) Filed: Aug. 31, 2021

(51) Int. Cl.
| | | |
|---|---|---|
| *A61L 2/10* | (2006.01) | |
| *F21L 4/02* | (2006.01) | |
| *F21L 4/08* | (2006.01) | |
| *F21L 4/04* | (2006.01) | |
| *F21V 7/04* | (2006.01) | |
| *F21V 21/40* | (2006.01) | |
| *F21V 23/04* | (2006.01) | |
| *F21V 7/00* | (2006.01) | |
| *F21Y 113/20* | (2016.01) | |
| *F21Y 115/10* | (2016.01) | |

(52) U.S. Cl.
CPC .............. *A61L 2/10* (2013.01); *F21L 4/025* (2013.01); *F21L 4/045* (2013.01); *F21L 4/085* (2013.01); *F21V 7/0075* (2013.01); *F21V 7/043* (2013.01); *F21V 21/406* (2013.01); *F21V 23/0492* (2013.01); *F21Y 2113/20* (2016.08); *F21Y 2115/10* (2016.08)

(58) Field of Classification Search
CPC . A61L 2/10; A61L 4/025; A61L 4/045; A61L 4/085; F21V 7/0075; F21V 7/043; F21V 21/406; F21V 23/0492
See application file for complete search history.

(56) References Cited

U.S. PATENT DOCUMENTS

| | | | | |
|---|---|---|---|---|
| 7,547,893 | B1 * | 6/2009 | Tantillo .................. | A61L 9/12 |
| | | | | 250/455.11 |
| 11,058,202 | B1 * | 7/2021 | Luu ..................... | F21V 33/0004 |
| 2013/0175460 | A1 * | 7/2013 | Farren ..................... | A23L 3/28 |
| | | | | 250/504 R |

FOREIGN PATENT DOCUMENTS

| | | | | | |
|---|---|---|---|---|---|
| CN | | 1330559 A | * | 1/2002 | ............... A61L 2/10 |
| CN | | 107208855 A | * | 9/2017 | ............... F21L 4/08 |

* cited by examiner

*Primary Examiner* — Anabel Ton
(74) *Attorney, Agent, or Firm* — Heedong Chae; Lucem, PC

(57) ABSTRACT

A portable illumination apparatus having a sterilizing function, the illumination apparatus including: a lamp unit which includes an illuminating light element on an interior side of the lamp unit; a base coupled to the lamp unit by a hinge; and a sterilizing light element located on the interior side of the lamp unit. When the lamp unit is in a closed position with the base, the lamp unit and the base meet at a boundary section to form a cylinder with a top and a bottom. Also, the boundary section is substantially mirror-symmetrical and at least partially U-shaped such that the lamp unit has a longest height line and a shortest height line. Additionally, the illuminating light element is arranged on or along the longest height line and the hinge is formed about the shortest height line.

20 Claims, 16 Drawing Sheets

PORTABLE ILLUMINATION APPARATUS HAVING STERTLIZING FUNCTION

FIELD OF THE INVENTION

The present invention relates to an illumination apparatus, and more particularly, a portable illumination apparatus having a sterilizing function.

BACKGROUND OF THE INVENTION

Conventional table lamps and desk lamps are commonly constructed with a single illumination unit that sits atop of a stand. Traditionally, the illumination unit was an incandescent filamentous light bulb. More recently, light emitting diodes (LEDs) have replaced the traditional light bulb as the illumination unit, one reason being the comparatively longer longevity of LEDs compared to light bulbs.

However, many of the conventional lamps are constructed to stand at same location atop of a table or desk, which severely limits their portability. With the advent of portable electronic devices that enables users to work or study at virtually any location, a portable lighting solution is needed for users to continue their work or study anywhere if the need arises. Additionally, if using a pad or paper, it is preferable that any writing implements can be stored to reduce clutter and that this storage is secure. Furthermore, it is preferable that these implements maintained clean, especially when used by children.

Therefore, to solve the above problems, various embodiments of a portable illumination apparatus having a sterilizing function are provided, as there is a need for a device that accomplishes these goals. This invention is directed to solve these problems and satisfy the long-felt need.

SUMMARY OF THE INVENTION

The present invention contrives to solve the disadvantages of the prior art. The present invention provides a portable illumination apparatus having a sterilizing function.

The object of the invention is to provide a portable illumination apparatus having a sterilizing function, the illumination apparatus including: a lamp unit which includes an illuminating light element on an interior side of the lamp unit; a base coupled to the lamp unit by a hinge; and a sterilizing light element located on the interior side of the lamp unit. When the lamp unit is in a closed position with the base, the lamp unit and the base meet at a boundary section to form a cylinder with a top and a bottom. Also, the boundary section is substantially mirror-symmetrical and at least partially U-shaped such that the lamp unit has a longest height line and a shortest height line. Additionally, the illuminating light element is arranged on or along the longest height line and the hinge is formed about the shortest height line.

Another object of the invention is to provide a portable illumination apparatus having a sterilizing function, the illumination apparatus including: a lamp unit which includes an illuminating light element on an interior side of the lamp unit; a base coupled to the lamp unit by a hinge; and a sterilizing light element located on the interior side of the lamp unit. When the lamp unit is in a closed position with the base, the lamp unit and the base meet at a boundary section to form a prism with a top and a bottom. Also, the boundary section is substantially mirror-symmetrical and at least partially U-shaped such that the lamp unit has a longest height line and a shortest height line. Additionally, the illuminating light element is arranged on or along the longest height line and the hinge is formed about the shortest height line.

The advantages of the present invention are: (1) a portable, and thus, transportable lighting to any location or setting; (2) a boundary section that not only forms a storage compartment to carry various writing or other productivity implements but also provides a long surface for the attachment of the illuminating light element to emit light over large surface area that is both wide and long; (3) a light source for not only reading, writing, or studying situations but also for emergency situations; (4) a pivoting handle to easily and conveniently carry the present invention; (5) different light intensities (i.e. brightness) for different situations that can be controlled instantly via a control panel; (6) when closed, the illumination apparatus sterilizes various writing and productivity implements stored therein; (7) when opened, the lighting from illumination apparatus may be adjusted to fit the user's reading angle preferences; and (8) the illumination apparatus is rechargeable from a variety of sources.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein.

DETAILED DESCRIPTION OF EMBODIMENTS OF THE INVENTION

Reference will now be made in detail to the preferred embodiments of the present invention, examples of which are illustrated in the accompanying drawings, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention.

Also, as used in the specification including the appended claims, the singular forms "a", "an", and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about", it will be understood that the particular value forms another embodiment.

Figure 1:
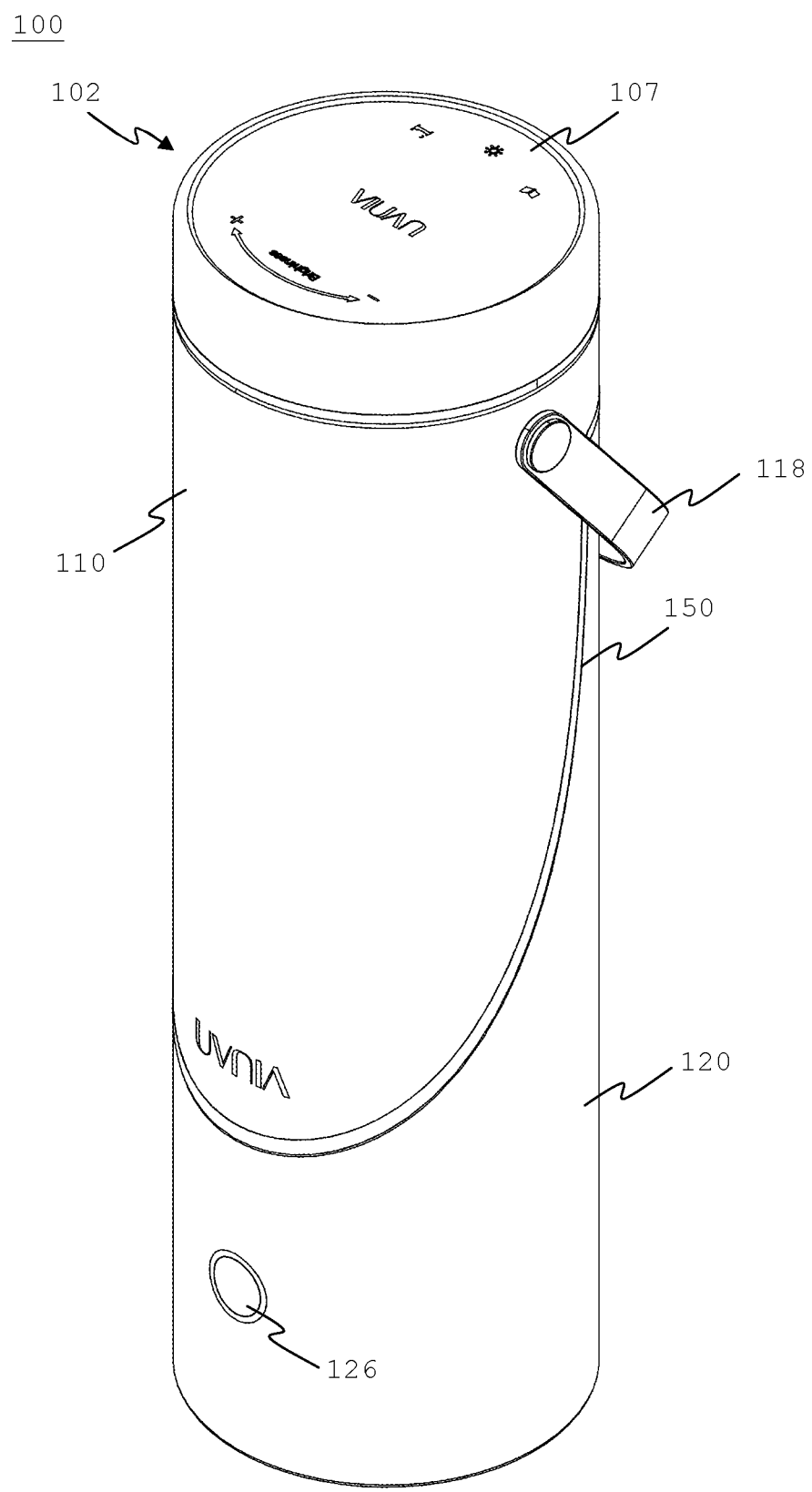
FIG. 1 shows a perspective view of an illumination apparatus having sterilizing function according to embodiments of the present invention.
Figure 2:
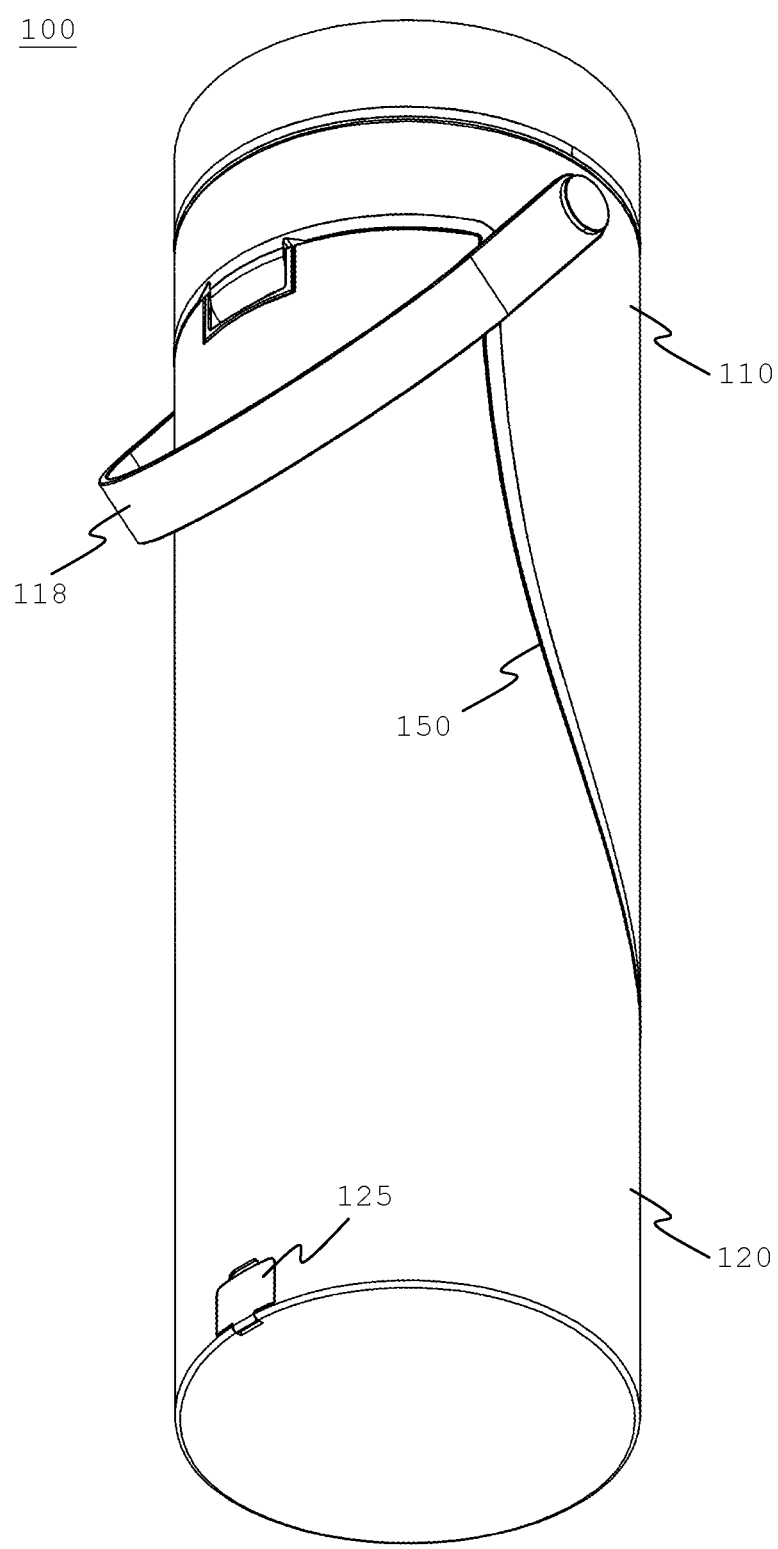
FIG. 2 shows a perspective view of the illumination apparatus according to embodiments of the present invention.
Figure 3:
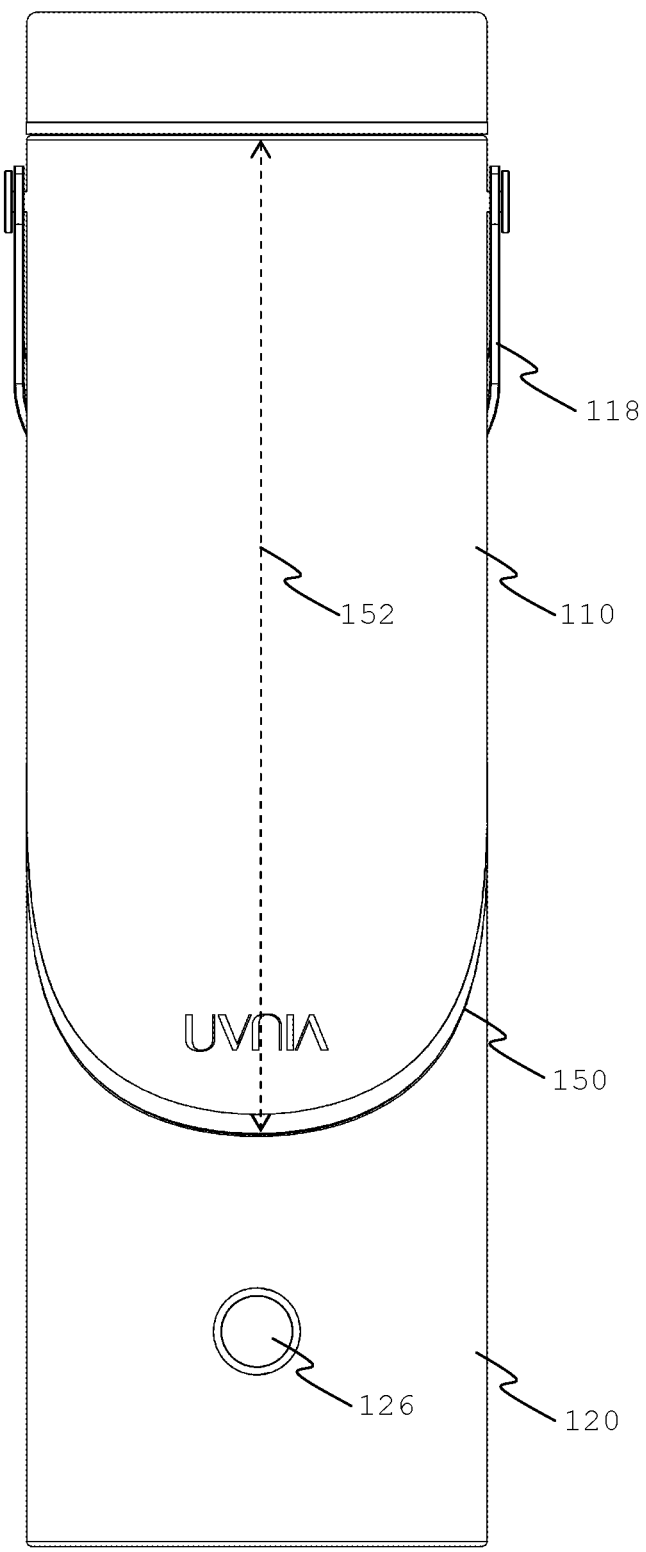
FIG. 3 shows a front view of the illumination apparatus according to embodiments of the present invention.
Figure 4:
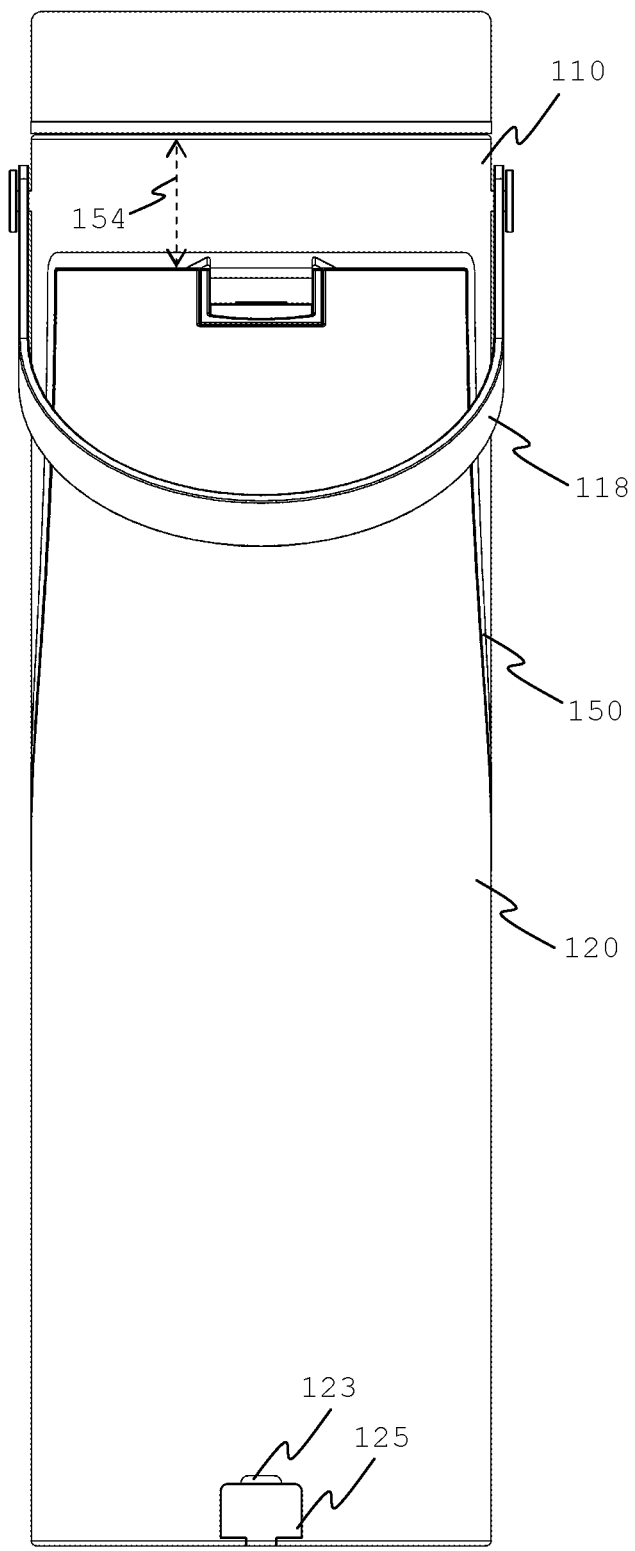
FIG. 4 shows a rear view of the illumination apparatus according to embodiments of the present invention.
Figure 5A:
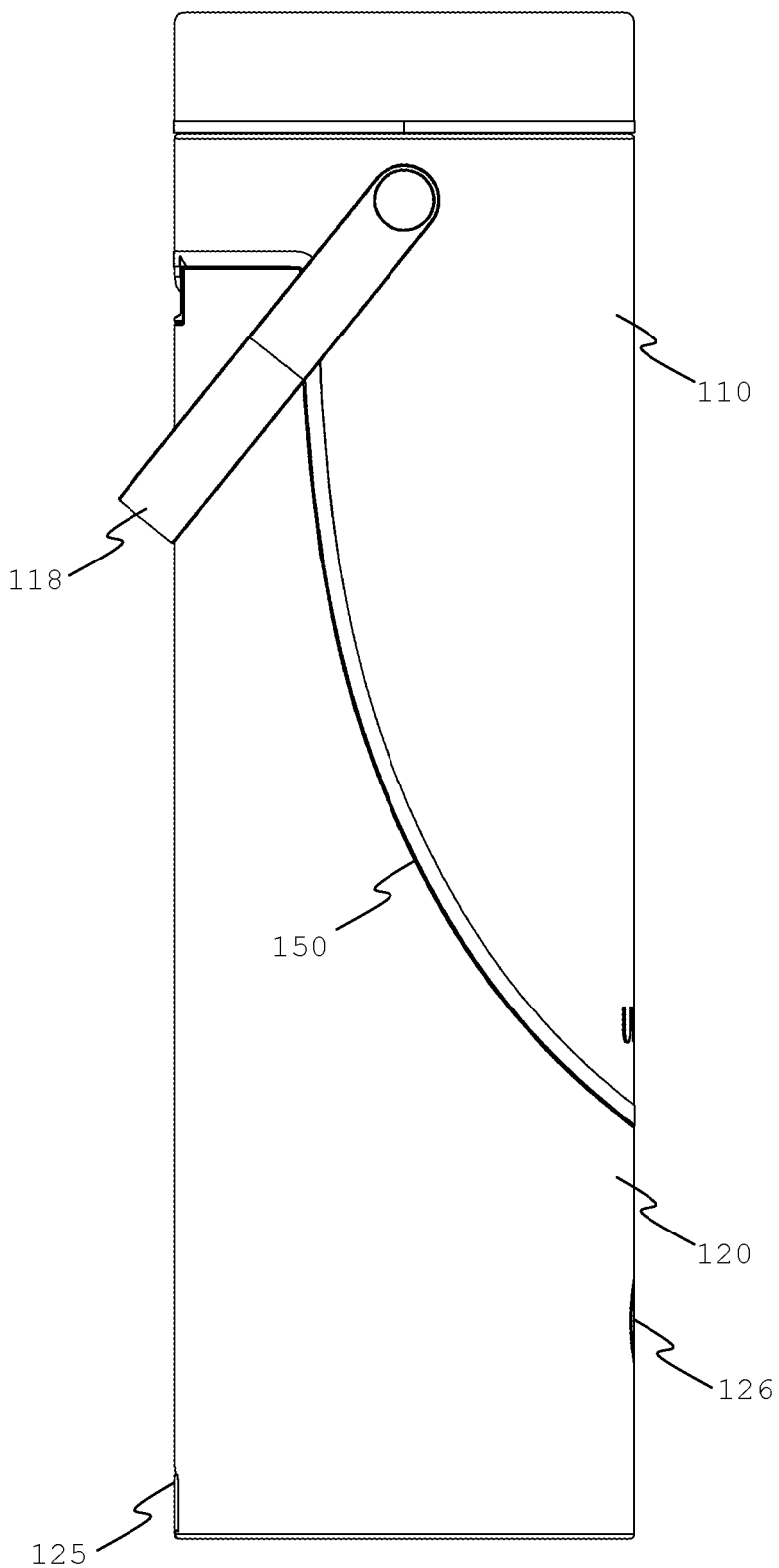
FIGS. 5A-B show side views of the illumination apparatus according to embodiments of the present invention.
Figure 5B:
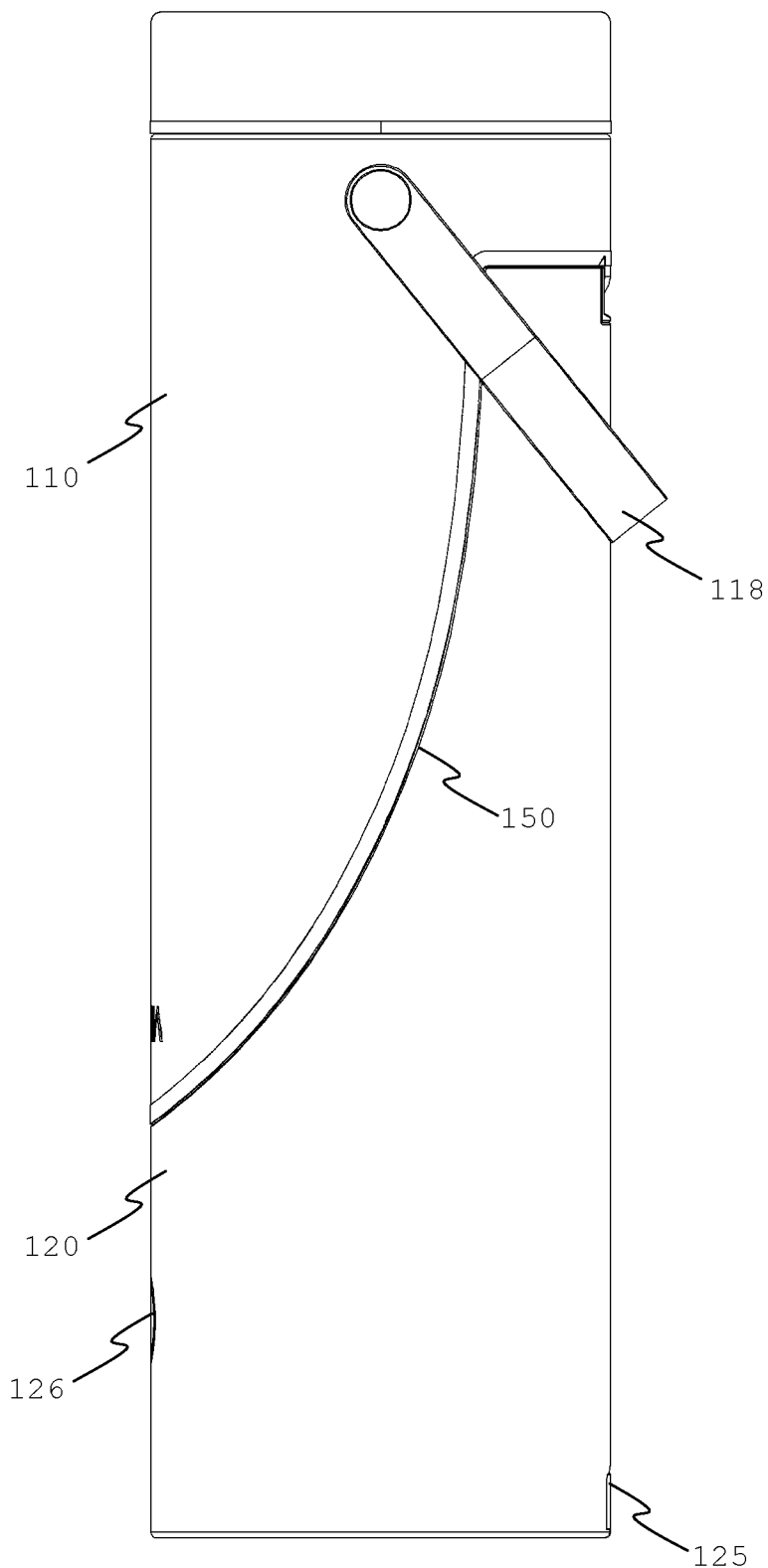
Figure 6:
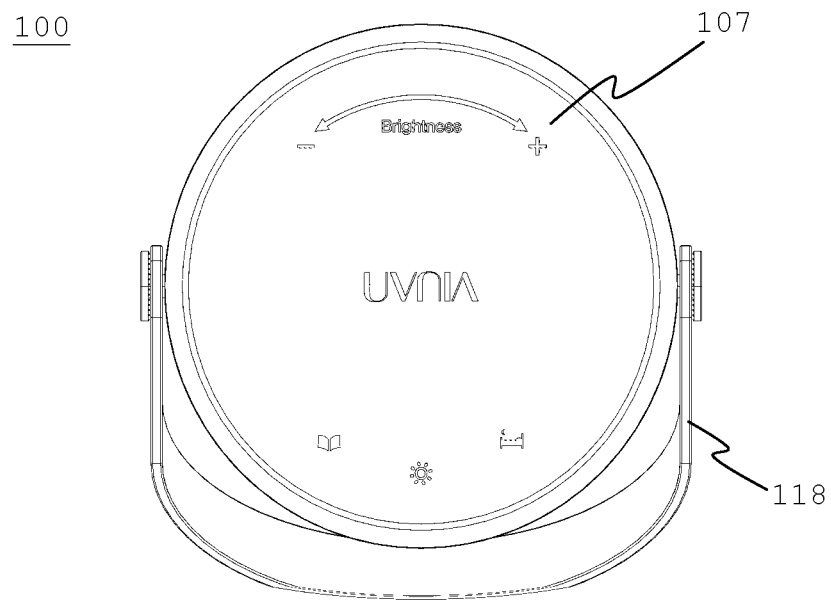
FIG. 6 shows a top view of the illumination apparatus according to embodiments of the present invention.
Figure 7:
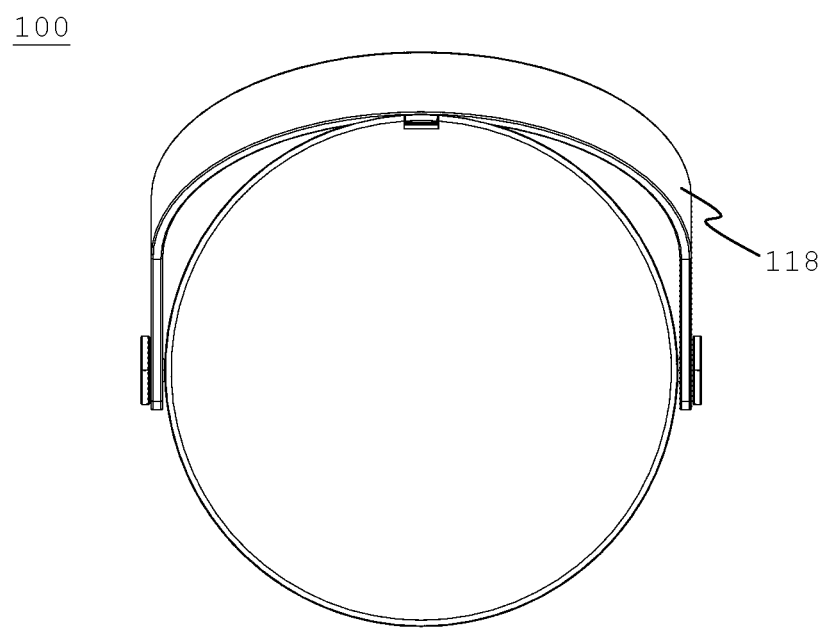
FIG. 7 shows a bottom view of the illumination apparatus according to embodiments of the present invention.
Figure 8:
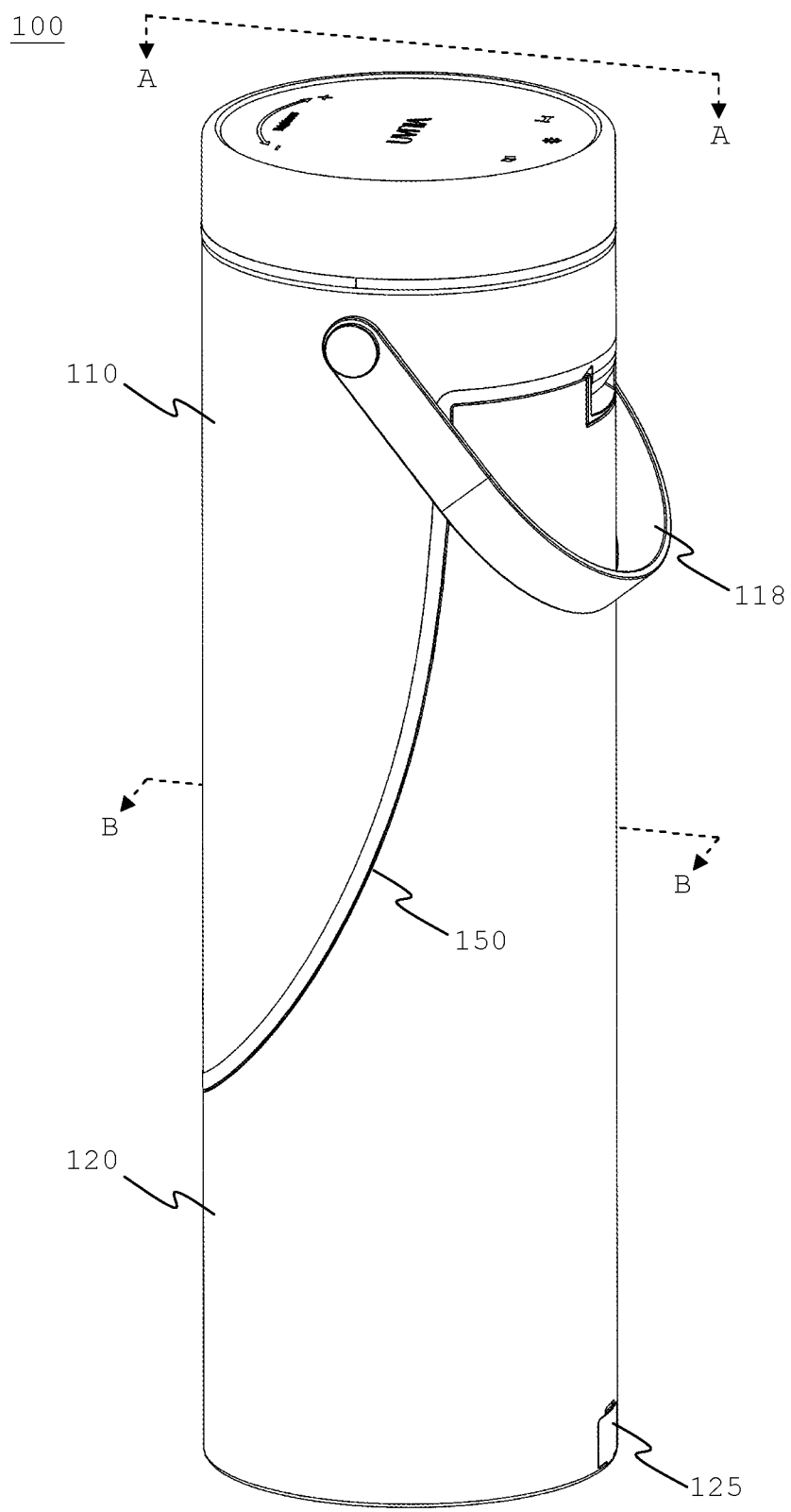
FIG. 8 shows a perspective view of the illumination apparatus according to embodiments of the present invention.
Figure 9:
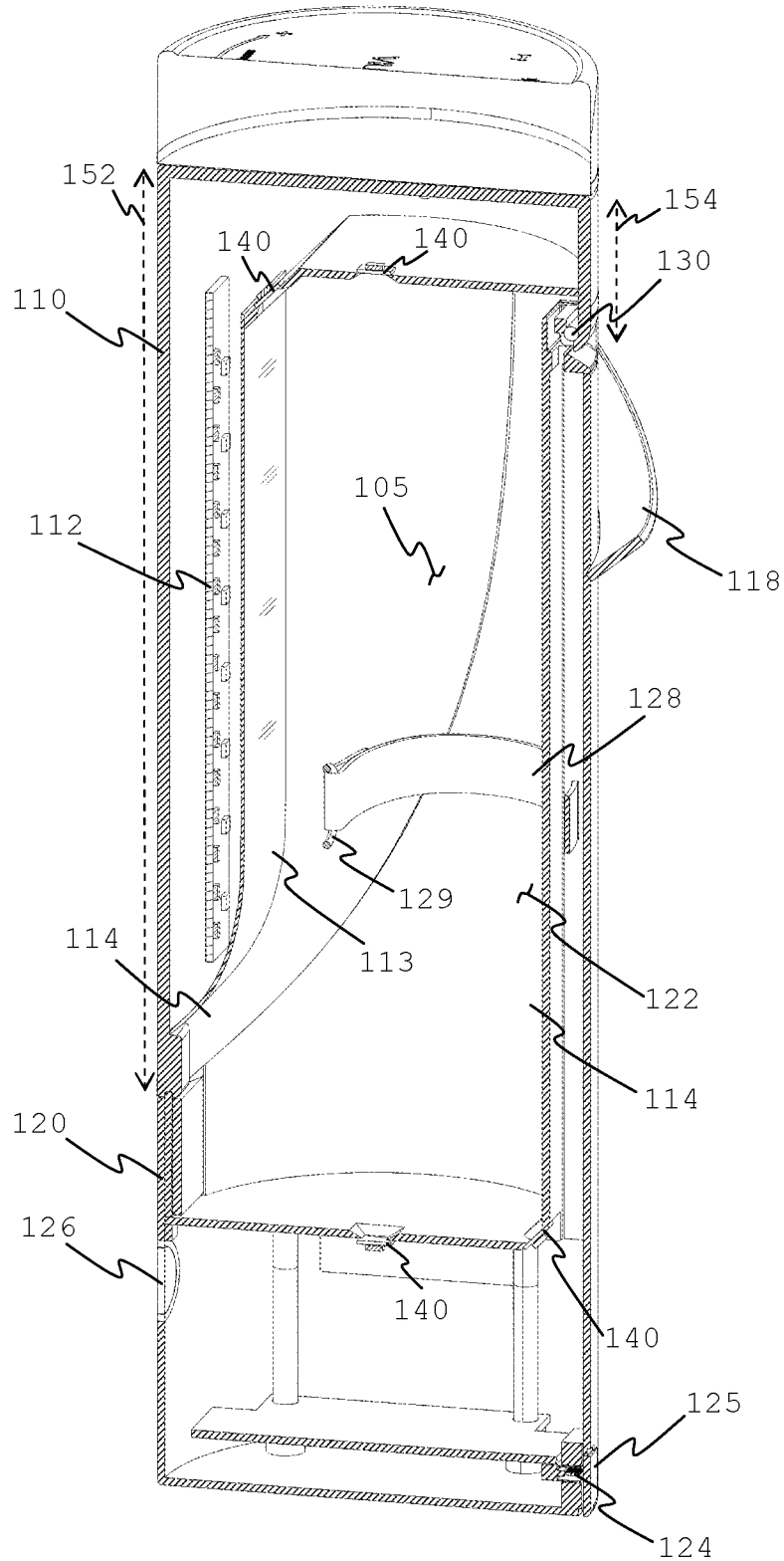
FIG. 9 shows a cross-sectional view, according to line A of FIG. 8, of the illumination apparatus according to embodiments of the present invention.
Figure 12A:
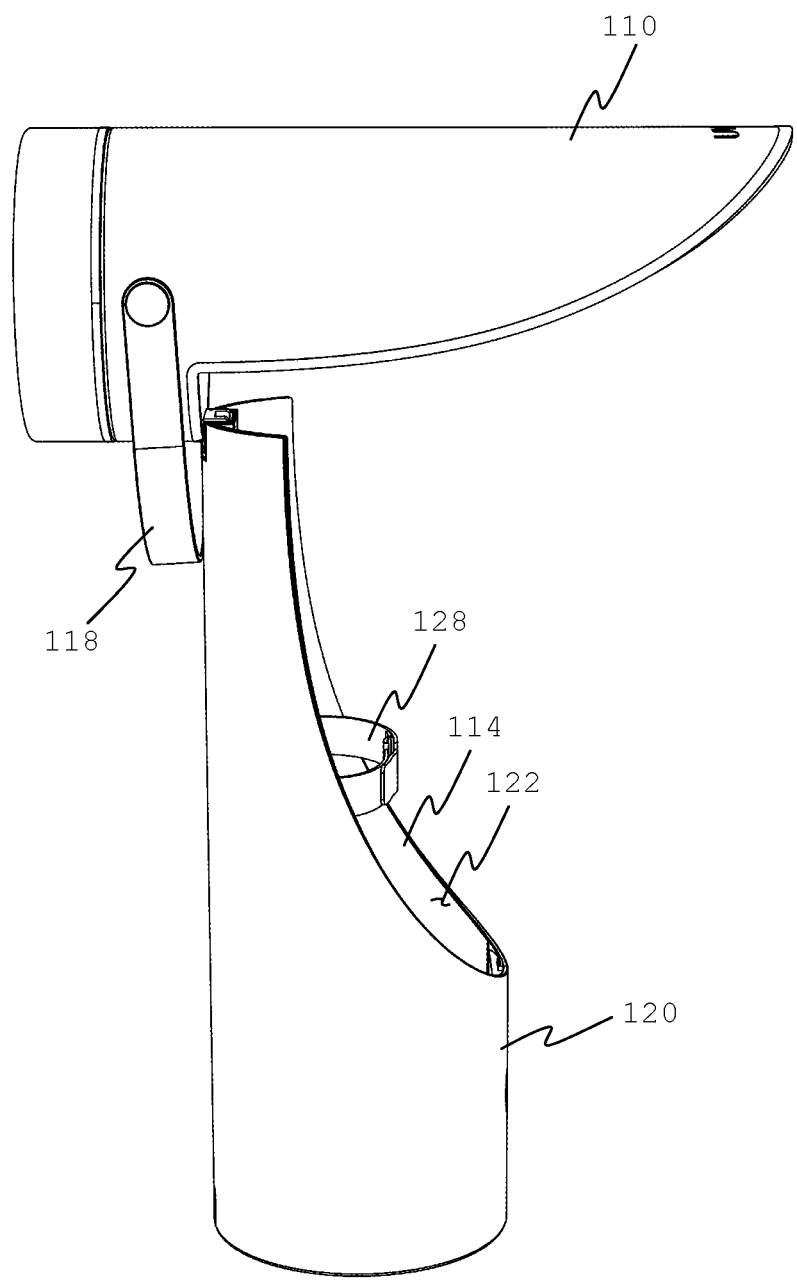
FIGS. 12A-B show perspective views of the illumination apparatus according to embodiments of the present invention.
Figure 12B:
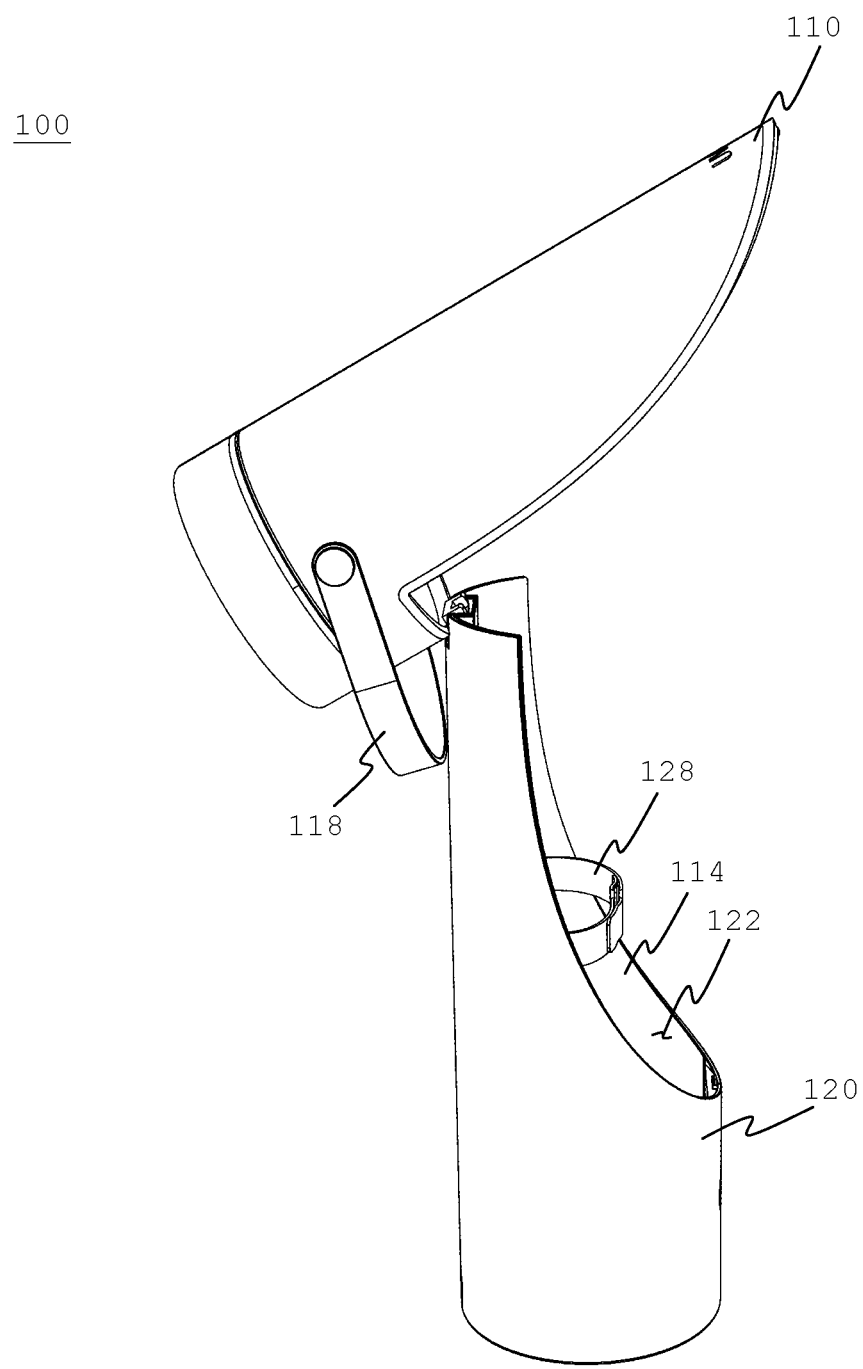
Figure 13:
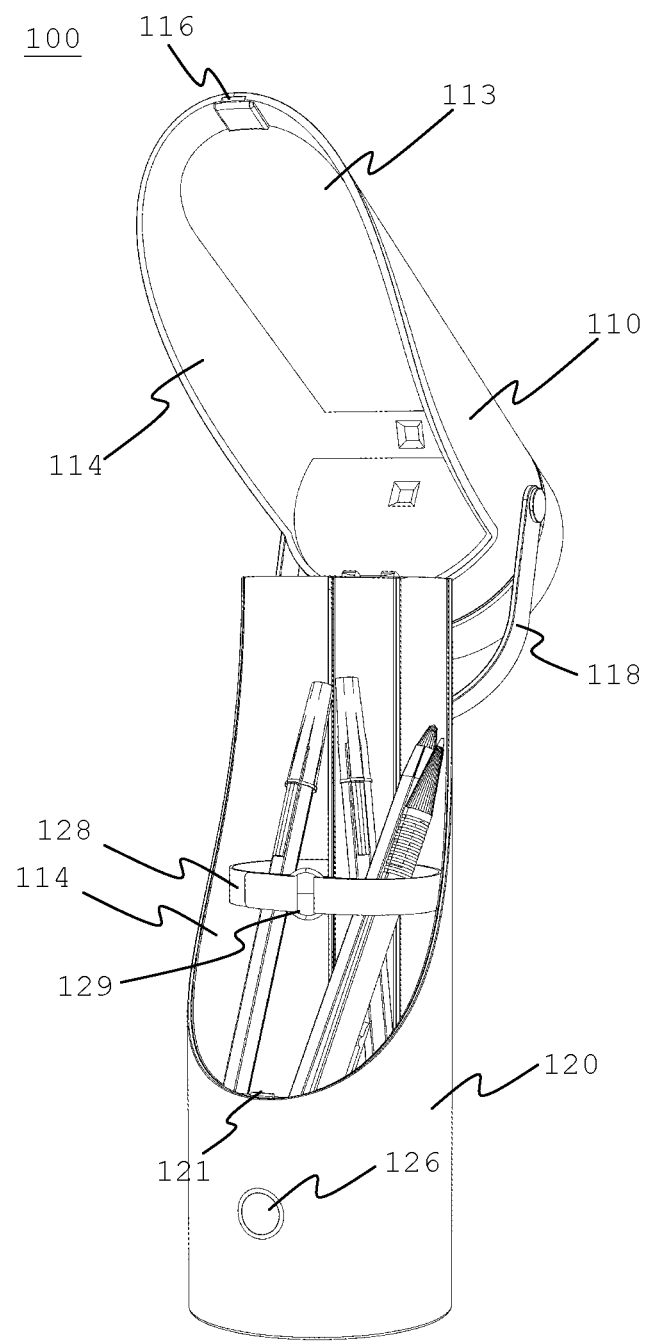
FIG. 13 shows a perspective view of the illumination apparatus according to embodiments of the present invention.

FIGS. 1-9 show a portable illumination apparatus (100) having a sterilizing function, the illumination apparatus (100) including: a lamp unit (110) which includes an illuminating light element (112) on an interior side of the lamp unit (110); a base (120) coupled to the lamp unit (110) by a hinge (130); and a sterilizing light element (140) located on the interior side of the lamp unit (110). As shown in FIGS. 1-9, when the lamp unit (110) is in a closed position with the base (120), the lamp unit (110) and the base (120) meet at a boundary section (150) to form a cylinder (102) with a top and a bottom, the outer side of this cylinder (102) is preferable stainless steel. Additionally, the boundary section (150) is substantially mirror-symmetrical and at least partially U-shaped such that the lamp unit (110) has a longest height line (152) and a shortest height line (154) as shown in FIGS. 3 and 4 respectively. Furthermore, as shown in FIG. 9, the illuminating light element (112) is arranged on or along the longest height line (152) and the hinge (130) is formed about the shortest height line (154). When the lamp unit (110) is in an opened position as shown in FIGS. 12 and 13, the illuminating light element (112) is turned on and when the lamp unit (110) is in a closed position, the sterilizing light element (140) is turned on.

Figure 10A:
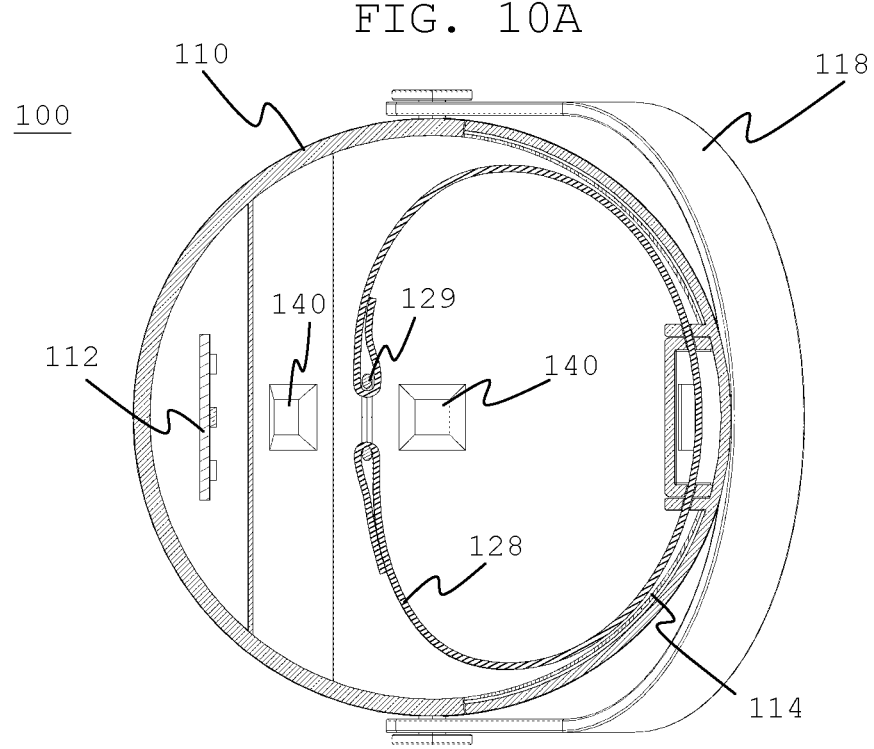
FIGS. 10A-B show cross-sectional views, according to line B of FIG. 8, of the illumination apparatus according to embodiments of the present invention.
Figure 10B:
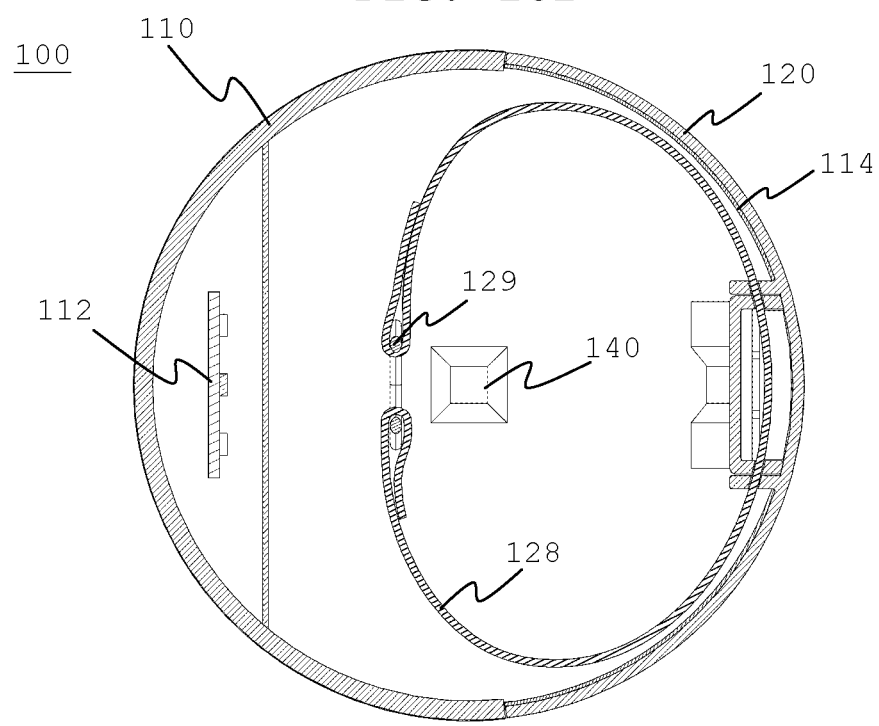

As shown in FIG. 9, the cylinder (102) forms a storage container (105) for storing items therein, and the base (120) includes a storage space (122). This interior area is preferably made from polycarbonate. FIGS. 12A-B, 13, and 14 further show the storage space (122) of the base (120) when the lamp unit (110) is in the opened position. To further secure the items within the cylinder (102), the base (120) further includes a storage strap (128) as shown in FIGS. 9 and 13. As shown in FIGS. 9 and 10A-B, the base (120) further a through-hole to permit the storage strap (128) to pass through the base (120) such that the base (120) holds up the storage strap (128) as shown in FIG. 9. The base (120) may further include a fastener (129) shown in FIGS. 9 and 10A-B that couples with both ends of the storage strap (128). As shown in FIGS. 12A-B and 13, this fastener (129) is optional.

The lamp unit (110) further includes a reflective material (114) on the interior side of the lamp unit (110). As shown in FIGS. 10A-B and 13, the base (120) further includes the reflective material (114). Ordered from highest reflectivity of UV light to the lowest, the reflective material (114) may be porous, sintered polytetrafluoroethylene (PTFE); aluminium; or stainless steel. When the lamp unit (110) is in the closed position and the sterilizing light element (140) is turned on, the sterilizing light from the sterilizing light element (140) may reflect off the reflective material (114) to promote sterilization of the base (120) and objects stored in the storing container (105), the objects mostly stored or held within the storage space (122) of the base (120) as shown in FIG. 13. As shown in FIGS. 9 and 10A-B, the sterilizing light element (140) may be a plurality of sterilizing light elements (140). At least one sterilizing light elements (140) is located towards the top of the interior side of the lamp unit (110), and at least one sterilizing light element (140) is located towards the bottom on an interior side of the base (120) as shown in FIG. 9. Also shown in FIG. 9, at least one sterilizing light element (140) is located at a side on an interior side of the lamp unit (110), and at least one sterilizing light element (140) is located at a side on an interior side of the base (120).

The illumination apparatus (100) further includes a control panel (107) and a battery (not shown). The battery supplies electricity to power the illuminating light element (112), the sterilizing light elements, the control panel (107), and any other additional electrical lighting or electricity-dependent elements that may be employed without departing from the spirit and scope of the disclosed embodiments of the present invention. The control panel (107), as shown in FIGS. 1, 6, 8, and 9, is installed at the top of the lamp unit (110) and the battery is installed at the bottom of the base (120). To charge the battery, the base (120) further includes a charging port (124) as shown in FIG. 9, which may be covered by a charging port cover (125) as shown in FIGS. 2, 4, 5A-B, 8, and 9. The charging port cover (125) is removably coupled to the base (120) either directly or indirectly. If indirectly, the base (120) may further include hinge piece (not shown), which may resilient, that connects the charging port cover (125) to the base (120). Additionally, the base (120) includes a notch (123) about the charging port cover (125), as shown in FIG. 4, which allows the user to displace the charging port cover (125) using their fingernail or any small tool to reveal and gain access to the charging port (124).

Figure 14:
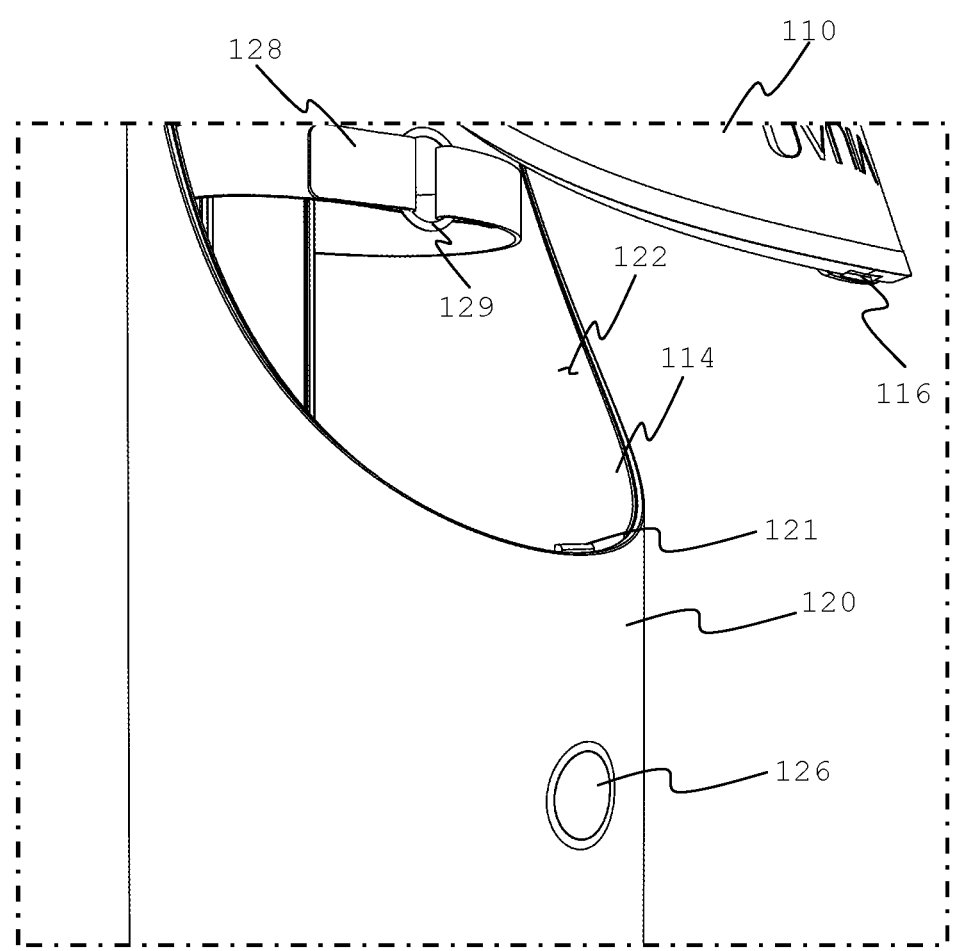
FIG. 14 shows a partial perspective view of the illumination apparatus according to embodiments of the present invention.

The base (120) includes a button (126) that, when pushed, releases the lamp unit (110) from the closed position with the base (120) and turns on the illuminating light element (112). To release the lamp unit (110) from the closed position, the base (120) further includes a protrusion (121) and the lamp unit (110) further includes a recess (116). The protrusion (121) is constructed to interact with the recess (116). The lamp unit (110) is in the closed position with the base (120) when the protrusion (121) is coupled to the recess (116) as shown in FIGS. 1-9. After pressing the button (126) to a sufficient depth, the the protrusion (121) slides down and is released from the recess (116) as shown in FIG. 14, which allows the lamp unit (110) to swing to the opened position as shown in FIGS. 12A-B. To turn on the illuminating light element (112), the button (126) is connected to a switch (not shown) that signals the illuminating light element (112) to turn on when the button (126) is pressed to open the lamp unit (110).

Figure 11:
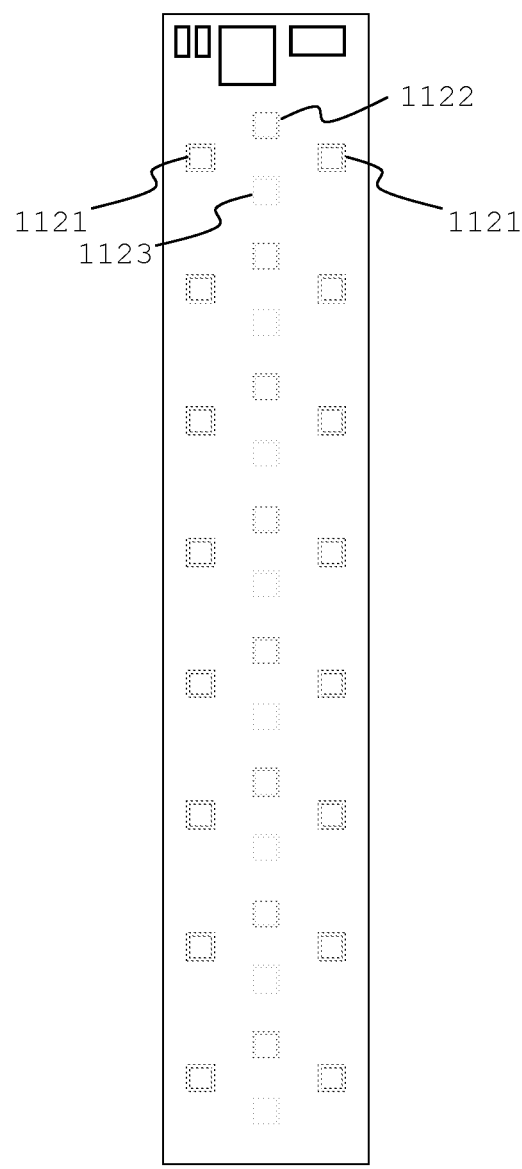
FIG. 11 showing an LED panel of the illumination apparatus according to embodiments of the present invention.

As shown in FIG. 9, the illuminating light element (112) is arranged in between both ends of the longest height line (152) and about outside of the shortest height line (154). Any light emitted from the illuminating light element (112) passes through the light panel (113) shown in FIGS. 9 and 13. The illuminating light element (112) includes an LED. More specifically, the LED includes at least one temperature color rating. Preferably, the LED includes the temperature color ratings of 5000K, 3000K, and 2700K to allow the user to cycle through (gradually) three different brightness ratings for the respective LEDs using the control panel (107). Other LED combinations with different color temperatures may be used in the illuminating light element (112). As shown in FIG. 11, the illuminating light element (112) is a board that includes arrayed LEDs of various color temperatures. Also shown, the lateral arrays include LEDs (1121) of 5000K and the medial array includes alternating LEDs (1122, 1123) of 3000K and 2000K respectively. Again, the illuminating light element (112) shown in FIG. 11 is for illustrative purposes, and thus, is not limited to the configuration as shown or the disclosed color temperatures of the LEDs (1121, 1122, 1123) considering that LEDs of other color temperatures, arrays, and combinations thereof may be easily added to or substituted with the above-mentioned LEDs (1121, 1122, 1123).

The sterilizing light element (140) emits ultraviolet-C (UV-C) light (wavelength of 200-280 nm). UV-C light is a known disinfectant for air, water, and non-porous surfaces, and it achieves this through electromagnetic irradiation where its wavelength band is within length range of wavelengths (250-270 nm) for microorganisms with the peak germicidal wavelength being 262 nm. Specifically, UV-C exposure induces damage to the genetic material of microorganisms and virus, which renders them inactive. Accordingly, UV-C is an effective disinfectant and, with regards to the illumination apparatus (100), provides a convenient means to disinfect the container space (105), the storage space (122), and the objects held therein when the lamp unit (110) is closed with the base (120). The reflective material (114) reflects and disperses the emission of the sterilizing light element (140) so that the emission sterilizes the maximal amount of surfaces of objects and areas within the illumination apparatus (100) when the lamp unit (110) is closed with the base (120), the emission of UV-C light lasting for a predetermined amount of time. If the lamp unit (110) is opened prior to the lapse of the predetermined amount of time, UV-C emission from the sterilizing light element (140) is turned off.

As shown in FIGS. 12A-B, in the opened position, the lamp unit (110) is angled about 90° to about 120° with respect to the base (120). The hinge (130), as shown in FIG. 9, allows the lamp unit (110) to pivot to the opened position at various angles. The hinge (130) is configured to allow the lamp unit (110) to stay opened at the desired angle until the user wishes to close the lamp unit (110) back to the base (120). The hinge (130) may be a self-opening spring-type hinge or the like.

As shown, the lamp unit (110) further includes a handle (118) to allow the illumination apparatus (100) to be carried from one location to another, thus increasing the convenience and portability of the illumination apparatus (100). The handle (118) is configured to be rotatably attached to the exterior surface of the lamp unit (110), so that the user may carry the illumination apparatus (100) like a bucket with a handles. The handle (118) may be made from natural or synthetic leather, or any other durable material.

Figure 15:
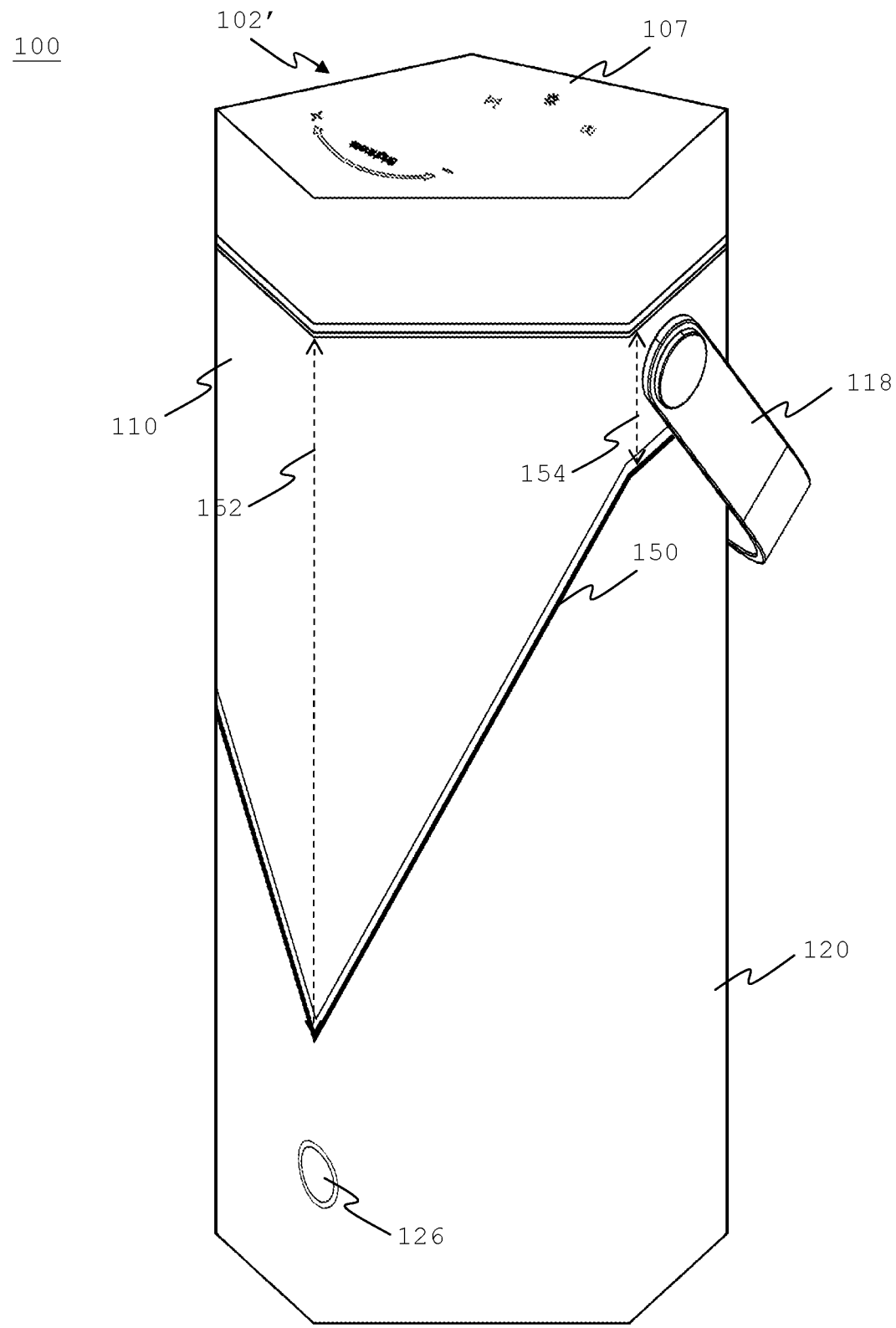
FIG. 15 shows a perspective view of the illumination apparatus according to embodiments of the present invention.

In an alternative embodiment, a portable illumination apparatus (100) is provided having a sterilizing function, the illumination apparatus (100) including a lamp unit (110) which includes an illuminating light element (112) on an interior side of the lamp unit (110); a base (120) coupled to the lamp unit (110) by a hinge (130); and a sterilizing light element (140) located on the interior side of the lamp unit (110). When the lamp unit (110) is in a closed position with the base (120), the lamp unit (110) and the base (120) meet at a boundary section (150) to form a prism (102') with a top and a bottom as shown in FIG. 15. The boundary section (150) is substantially mirror-symmetrical and at least partially U-shaped such that the lamp unit (110) has a longest height line (152) and a shortest height line (154). Additionally, the illuminating light element (112) is arranged on or along the longest height line (152) and the hinge (130) is formed about the shortest height line (154).

Similar to the previous embodiment, when the lamp unit (110) is in an opened position, the illuminating light element (112) is turned on, and when the lamp unit (110) is in a closed position, the sterilizing light element (140) is turned on. Likewise to the previous embodiment, the illuminating light element (112) is arranged between both ends of the longest height line (152) and about outside of the shortest height line (154).

The prism (102') that is shown in FIG. 15 forms a storage container (105) for storing items therein similar to that shown in FIG. 9 except for the prismatic shape of the illumination apparatus (100) of this embodiment. Additionally, the base (120) includes a storage space (122). The lamp unit (110) further includes a reflective material (114) on the interior side of the lamp unit (110), and the base (120) further includes the reflective material (114). The reflective material (114) may be may be porous, sintered polytetrafluoroethylene (PTFE); aluminium; or stainless steel as disclosed earlier. The sterilizing light element (140) is a plurality of sterilizing light elements (140) similar to that shown in FIG. 9. As in the previous embodiment, at least one sterilizing light element (140) is located at the top on the interior side of the lamp unit (110), at least one sterilizing light element (140) is located at the bottom on an interior side of the base (120), at least one sterilizing light element (140) is located at a side on an interior side of the lamp unit (110), and at least one sterilizing light element (140) is located at a side on an interior side of the base (120). Similar to the previous embodiment, The sterilizing light elements (140) in this embodiment emit UV-C light (wavelength of 200-280 nm) for disinfecting purposes, the action of which and its timing were explained in detail in the previous embodiment.

The illuminating light element (112) is similarly constructed here as in the previous embodiment. In this embodiment, the illuminating light element (112) includes an LED. More specifically, the LED includes at least one temperature color rating. Preferably, the LED includes the temperature color ratings of 5000K, 3000K, and 2700K to allow the user to cycle through (gradually) three different brightness ratings for the respective LEDs using the control panel (107). Other LED combinations with different color temperatures may be used in the illuminating light element (112). In this embodiment, the illuminating light element (112) is a board that includes LEDs of various color temperatures in arrays as shown in FIG. 11. The lateral arrays shown in FIG. 11 include LEDs (1121) of 5000K and the medial array includes alternating LEDs (1122, 1123) of 3000K and 2000K respectively. Again, the illuminating light element (112) shown in FIG. 11 is for illustrative purposes, and thus, is not limited to the configuration as shown nor limited to the disclosed color temperatures of the LEDs (1121, 1122, 1123) considering that LEDs of other color temperatures, arrays, and combinations thereof may be easily added to or substituted with the above-mentioned LEDs (1121, 1122, 1123).

The illumination apparatus (100) further includes a control panel (107) as shown in FIG. 15 and a battery (not shown). The control panel (107) is installed at the top of the lamp unit (110) and the battery (not shown) is installed at the bottom of the base (120). The battery supplies electricity to power the illuminating light element (112), the sterilizing light elements, the control panel (107), and any other additional electrical lighting or electricity-dependent elements that may be employed without departing from the spirit and scope of the disclosed embodiments of the present invention. The base (120) further includes a charging port (124) for charging the battery (108) similar to the charging port (124), which also may be covered by a charging port cover (125) as shown in FIG. 9. The charging port cover (125) is removably coupled to the base (120) either directly or indirectly. For indirect coupling, the base (120) may further include hinge piece (not shown), which may resilient, that connects the charging port cover (125) to the base (120). Additionally, the base (120) includes a notch (123) about the charging port cover (125)m similar to that shown in FIG. 4, which allows the user to displace the charging port cover (125) using their fingernail or any small tool to reveal and gain access to the charging port (124).

Also shown in FIG. 15, the base (120) further includes a button (126) that, when pushed, releases the lamp unit (110) from the closed position with the base (120) and turns on the illuminating light element (112). To release the lamp unit (110) from the closed position, the base (120) further includes a protrusion (121) and the lamp unit (110) further includes a recess (116) as similarly shown in FIG. 14. The protrusion (121) is constructed to interact with the recess (116). The lamp unit (110) is in the closed position with the base (120), as shown in FIG. 15, when the protrusion (121) is coupled to the recess (116). After pressing the button (126) to a sufficient depth, the protrusion (121) slides down and is released from the recess (116), which allows the lamp unit (110) to swing to the opened position as similarly shown in FIGS. 12A-B. To turn on the illuminating light element (112), the button (126) is connected to a switch (not shown) that signals the illuminating light element (112) to turn on when the button (126) is pressed to open the lamp unit (110).

While the invention has been shown and described with reference to different embodiments thereof, it will be appreciated by those skilled in the art that variations in form, detail, compositions and operation may be made without departing from the spirit and scope of the invention as defined by accompanying claims.

What is claimed is:

1. A portable illumination apparatus having a sterilizing function, the illumination apparatus comprising:
   a lamp unit which includes an illuminating light element on an interior side of the lamp unit;
   a base coupled to the lamp unit by a hinge; and
   a sterilizing light element located on the interior side of the lamp unit,
   wherein, when the lamp unit is in a closed position with the base, the lamp unit and the base meet at a boundary section to form a cylinder with a top and a bottom,
   wherein the boundary section is substantially mirror-symmetrical about an axis and at least partially U-shaped such that the lamp unit has a front portion and a rear portion, and
   wherein the illuminating light element is arranged on the front portion of the lamp unit about on or along the axis and the hinge is formed about the rear portion of the lamp unit.

2. The illumination apparatus of claim 1, wherein, when the lamp unit is in an opened position, the illuminating light element is turned on, and
   wherein, when the lamp unit is in a closed position, the sterilizing light element is turned on.

3. The illumination apparatus of claim 1, wherein the illuminating light element is arranged about below the hinge.

4. The illumination apparatus of claim 1, wherein the cylinder forms a storage container for storing items therein, and
   wherein the base includes a storage space.

5. The illumination apparatus of the claim 4, wherein the lamp unit further includes a reflective material on the interior side of the lamp unit, and
   wherein the base further includes the reflective material.

6. The illumination apparatus of claim 5, wherein the sterilizing light element is a plurality of sterilizing light elements,
   wherein at least one sterilizing light element is located at the top on the interior side of the lamp unit, and
   wherein at least one sterilizing light element is located at the bottom on an interior side of the base.

7. The illumination apparatus of claim 6, wherein at least one sterilizing light element is located at a side on an interior side of the lamp unit, and
   wherein at least one sterilizing light element is located at a side on an interior side of the base.

8. The illumination apparatus of claim 4, further comprising a control panel and a battery,
   wherein the control panel is installed at the top of the lamp unit and the battery is installed at the bottom of the base.

9. The illumination apparatus of claim 8, wherein the base further includes a charging port for charging the battery.

10. The illumination apparatus of claim 4, wherein the base includes a button to release the lamp unit from the closed position with the base and turn on the illuminating light element.

11. The illumination apparatus of claim 10, wherein the base further includes a protrusion,
    wherein the lamp unit further includes a recess, and
    wherein the lamp unit is in the closed position when the protrusion is coupled to the recess, and the lamp unit is in the opened position when the protrusion is released from the recess after the button has been pressed.

12. The illumination apparatus of claim 4, wherein, in the opened position, the lamp unit is angled about 90° to about 120° with respect to the base, and
    wherein the hinge allows the lamp unit to pivot to the opened position.

13. The illumination apparatus of claim 4, wherein the illuminating light element includes an LED, and
    wherein the sterilizing light element emits UV-C light.

14. The illumination apparatus of claim 1, wherein the lamp unit further includes a handle to allow the illumination apparatus to be carried, and
    wherein the handle is rotatably attached to the exterior surface of the lamp unit.

15. A portable illumination apparatus having a sterilizing function, the illumination apparatus comprising:
    a lamp unit which includes an illuminating light element: on an interior side of the lamp unit;

a base coupled to the lamp unit by a hinge; and a sterilizing light element located on the interior side of the lamp unit, wherein, when the lamp unit is in a closed position with the base, the lamp unit and the base meet at a boundary section to form a prism with a top and a bottom, wherein the boundary section is substantially mirror-symmetrical about an axis and at least partially U-shaped such that the lamp unit has a front portion and a rear portion, and wherein the illuminating light element is arranged on the front portion of the lamp unit on or along the the axis and the hinge is formed about the rear portion of the lamp unit.

16. The illumination apparatus of claim 15, wherein, when the lamp unit is in an opened position, the illuminating light element is turned on, and wherein, when the lamp unit is in a closed position, the sterilizing light element is turned on.

17. The illumination apparatus of claim 15, wherein the illuminating light element is arranged about below the hinge.

18. The illumination apparatus of claim 15, wherein the prism forms a storage container for storing items therein, wherein the base includes a storage space, wherein the lamp unit further includes a reflective material on the interior side of the lamp unit, and wherein the base further includes the reflective material.

19. The illumination apparatus of claim 18, wherein the sterilizing light element is a plurality of sterilizing light elements, wherein at least one sterilizing light element is located at the top on the interior side of the lamp unit, wherein at least one sterilizing light element is located at the bottom on an interior side of the base, wherein at least one sterilizing light element is located at a side on an interior side of the lamp unit, and wherein at least one sterilizing light element is located at a side on an interior side of the base.

20. The illumination apparatus of claim 18, further comprising a control panel and a battery, wherein the control panel is installed at the top of the lamp unit and the battery is installed at the bottom of the base, and wherein the base further includes a charging port for charging the battery.

* * * * *